United States Patent [19]
Pestellini et al.

[11] Patent Number: 4,551,451
[45] Date of Patent: Nov. 5, 1985

[54] TRICYCLIC DERIVATIVES OF 5,6-DIHYDRO-11H-DIBENZO (B,E) AZEPIN-6-ONE HAVING PHARMACOLOGICAL ACTIVITY

[75] Inventors: Vittorio Pestellini; Mario Ghelardoni; Alessandro Giolitti; Giovanna Volterra, all of Florence; Martino Furio, Rome; Alberto Meli, Florence, all of Italy

[73] Assignee: A. Menarini S.a.S., Italy

[21] Appl. No.: 639,687

[22] Filed: Aug. 10, 1984

Related U.S. Application Data

[63] Continuation of Ser. No. 475,327, Mar. 14, 1983, abandoned.

[30] Foreign Application Priority Data

Mar. 15, 1982 [IT] Italy ................................. 9356 A/82

[51] Int. Cl.$^4$ ...................... A61K 31/53; C07D 223/20
[52] U.S. Cl. ............................... 514/217; 260/239.3 T
[58] Field of Search ................... 260/239.3 T; 424/244

[56] References Cited

U.S. PATENT DOCUMENTS 3,431,257  3/1969  Aichinger et al. ........... 260/239.3 T
4,336,192  6/1982  Steiner et al. ................ 260/239.3 T

OTHER PUBLICATIONS

Jilek et al., "Coll. Czech. Chem. Comm.", vol. 30, pp. 445–462, (1965).
Morconi et al., "J. Org. Chem.", vol. 37, pp. 208–215, (1972).
Eiden et al., "Arch. Pharm.", vol. 312, pp. 662–669, (1979).
Ballantine et al., "J. Chem. Soc.", (1964), pp. 3323–3330.
Noller, "Chemistry of Organic Compounds", (2nd Edition), (1957), pp. 199, 244, 319.

*Primary Examiner*—Robert T. Bond
*Attorney, Agent, or Firm*—McGlew and Tuttle

[57] ABSTRACT

A pharmacologically active compound has the general formula

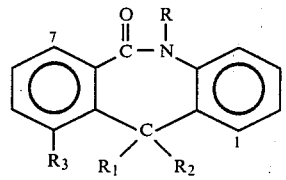

in which R is a hydrogen atom or an alkyl group containing from 1 to 4 carbon atoms; $R_1$ and $R_2$, which can be different, represent a hydrogen atom, a hydroxyl group, an alkyl group, an alkoxy group, an arylalkyl group, or an arylalkoxy group, or can jointly represent an oxygen atom or a CHCOOR$_1'$ group where $R_1'$ is a hydrogen atom or an alkyl group; and $R_3$ represents a hydrogen or halogen atom or an alkyl, NH$_2$, NO$_2$, NHCO-alkyl, NHCO-aryl, NHCONH-alkyl or NHCOHN-aryl group.

These compounds act on the central nervous system and have an anti-convulsant sedative activity.

18 Claims, No Drawings

TRICYCLIC DERIVATIVES OF 5,6-DIHYDRO-11H-DIBENZO (B,E) AZEPIN-6-ONE HAVING PHARMACOLOGICAL ACTIVITY

This is a continuation of parent application, Ser. No. 475,327, filed Mar. 14, 1983, and now abandoned.

The invention relates to new 5,6-dihydro-11H-dibenzo (b,e) azepin-6-ones which are pharmacologically active particularly on the central nervous system, and further relates to pharmaceutical preparations containing said substances and to methods for producing and utilising said 5,6-dihydro-11H-dibenzo (b,e) azepin-6-ones.

It is widely known that tricyclic derivatives of 5,6-dihydro-11H-dibenzo (b,e) azepin-6-one are active on the central nervous system, but it is also known that said compounds either have undesirable side-effects or a limited time action.

This invention relates to new derivatives which act on the central nervous system and which have protracted activity together with lesser side-effects.

The compounds according to the present invention are of general formula I

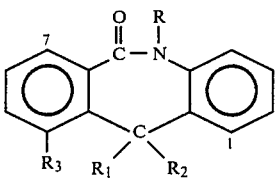

in which R is a hydrogen atom or an alkyl group containing from 1 to 4 carbon atoms; $R_1$ and $R_2$, which can be different, represent a hydrogen atom, a halogen atom, a hydroxyl group, an alkyl group such as alkyl containing 1 to 8 carbon atoms, an alkoxy group such as alkoxy containing 1 to 8 carbon atoms, an arylalkyl group such as phenyl lower alkyl or an arylalkoxy group, or can jointly represent an oxygen atom or a=CHCOOR$_1'$ group, where $R_1'$ is a hydrogen atom or an alkyl group such as alkyl containing 1 to 4 carbon atoms; and $R_3$ represents a hydrogen or halogen atom or an alkyl, $NO_2$, $NH_2$, NHCO-alkyl such as NHCO-lower alkyl, NHCO-aryl as NHCO-phenyl, NH—CONH-alkyl such as NH—CONH-lower alkyl or NH—CO—NH—aryl such as —NH—CO—NH—phenyl, group.

Some examples of the compounds of general formula I which lie within the present invention are as follows:

(1) 10-acetamino-5,6-dihydro-11H-dibenzo (b,e) azepine-6,11-dione
(In formula I, R is H, $R_1$ and $R_2$ are O, $R_3$ is NHCOCH$_3$)
M.P. 270°–2° C.
I.R. (nujol), $\nu$ (cm$^{-1}$): 1685, 1655 (CO).
H—NMR (DMSO), $\delta$ (p.p.m.) 2.0 (s, CH$_3$) 6.95–8.0. (m, C$_6$H$_4$+C$_6$H$_3$) 10.05 (s, NH).

(2) N-methyl-N'[5,6-dihydro-6,11-dione-11H-dibenzo (b,e) azepin-10-yl]urea
(In formula I, R is H, $R_1$ and $R_2$ are O, $R_3$ is NHCONHCH$_3$)
M.P. 250°–2° C.
I.R. (nujol), $\nu$ (cm$^{-1}$): 1665, 1640 (CO).

(3) 5,11-dimethyl-11-hydroxy-5,6-dihydro-11H-dibenzo (b, e) azepin-6-one
(In formula I, R is CH$_3$, $R_1$ is OH, $R_2$ is CH$_3$, $R_3$ is H)
M.P. 200°–202° C.
I.R. (nujol), $\nu$ (cm$^{-1}$): 3390 (OH) 1610 (CO).
H—NMR (DMSO), $\delta$ (p.p.m.) 2.05 (s, CH$_3$) 3.8 (s, CH$_3$).
7.10–8.25 (m, 2×C$_6$H$_4$).

(4) 10-acetamino-5-methyl-5,6-dihydro-11H-dibenzo (b,e) azepine-6,11-dione
(In formula I, R is CH$_3$, $R_1$ and $R_2$ are O, $R_3$ is NHCOCH$_3$) M.P. 199°–201° C.
I.R. (nujol), $\nu$ (cm$^{-1}$): 3320 (OH) 1655, 1645 (CO).
H—NMR (DMSO), $\delta$ (p.p.m.) 2.0 (s, CH$_3$) 3.4 (s, CH$_3$).
7.0–7.9 (m, C$_6$H$_4$+C$_6$H$_3$) 9.75 (s, NH).

(5) 5-methyl-11-ethoxy-5,6-dihydro-11H-dibenzo (b,e) azepin-6-one
(In formula I, R is CH$_3$, $R_1$ is H, $R_2$ is OEt, $R_3$ is H)
M.P. 98°–100° C.
I.R. (nujol), $\nu$ (cm$^{-1}$): 1640 (CO).

(6) 5-methyl-5,6-dihydro-6-one-11H-dibenzo (b,e) azepin-11-ylidene ethyl acetate
(In formula I, R is CH$_3$, $R_1$ and $R_2$ are CHCOOEt, $R_3$ is H)
M.P. 123°–5° C.
I.R. (nujol), $\nu$ (cm$^{-1}$): 1720, 1640 (CO).
H—NMR (CDCl$_3$), $\delta$ (p.p.m.): 1.1 (t, CH$_3$) 3.55 (s, CH$_3$).
4.10 (q, CH$_2$) 6.10 (s, CH) 7.15–8.10 (m, 2×C$_6$H$_4$)

(7) 10-benzoylamino-5,6-dihydro-11H-dibenzo (b,e) azepine-6,11-dione
(In formula I, R is H, $R_1$ and $R_2$ are O, $R_3$ is NHCOC$_6$H$_5$)
M.P. 280°–3° C.
I.R. (nujol), 84 (cm$^{-1}$): 1685, 1660 (CO).
H—NMR (DMSO), $\delta$ (p.p.m.): 7.0–8.10 (m, C$_6$H$_5$+2×C$_6$H$_4$).

(8) N-phenyl-N'[5,6-dihydro-6,11-dione-11H-dibenzo (b,e) azepin-10-yl]urea
(In formula I, R is H, $R_1$ and $R_2$ are O, $R_3$ is NHCONH—C$_6$H$_5$)
M.P. 277°–80° C.
I.R. (nujol), $\nu$ (cm$^{-1}$): 1665, 1640 (CO).

(9) 11-benzyl-11-hydroxy-5-methyl-5,6-dihydro-11H-dibenzo (b,e) azepin-6-one
(In formula I, R is CH$_3$, $R_1$ is OH, $R_2$ is CH$_2$C$_6$H$_5$, $R_3$ is H)
M.P. 169°–72° C.
I.R. (nujol), $\nu$ (cm$^{-1}$): 3410 (OH) 1610 (CO).

(10) 10-benzoylamino-5-methyl-5,6-dihydro-11H-dibenzo (b,e) azepine-6,11-dione
(In formula I, R is CH$_3$, $R_1$ and $R_2$ are O, $R_3$ is NHCOC$_6$H$_5$)
M.P. 173°–5° C.
I.R. (nujol), $\nu$ (cm$^{-1}$): 3305 (NH) 1675, 1620 (CO).
H—NMR (DMSO), $\delta$ (p.p.m.): 3.4 (s, CH$_3$) 7.05–7.95.
(m, C$_6$H$_5$+C$_6$H$_4$+C$_6$H$_3$).

(11) 11-octyloxy-5-methyl-5,6-dihydro-11H-dibenzo (b,e) azepin-6-one
(In formula I, R is CH$_3$, $R_1$ is H, $R_2$ is OC$_8$H$_{17}$, $R_3$ is H)
M.P. 205° C./0.3 mm Hg.
I.R. (nujol), $\nu$ (cm$^{-1}$): 1640 (CO).

This invention also relates to processes for synthesising the products of general formula I. The following synthesis methods are described by way of non-limiting example:

EXAMPLE 1

N-methyl-N']5,6-dihydro-6,11-dione-11H-dibenzo (b,e) azepin-10-yl]urea 1.5 g of 10-amino-5,6-dihydro-11H-dibenzo (b,e)azepine-6,11-dione, 3 ml of methyl isocyanate and 10 ml of dioxane are left at ambient temperature for 48 hours, the mixture is then poured into petroleum ether, and the precipitate formed is filtered off. The product has a M.P. of 250°-2° C. on crystallising from isopropanol.

EXAMPLE 2

5,11-dimethyl-11-hydroxy-5,6-dihydro-11H-dibenzo (b,e) azepin-6-one 10 ml of methyl iodide in 50 ml of anhydrous ethyl ether are added to 3.3 g of magnesium chips in anhydrous ethyl ether at a rate such as to maintain a slight reflux.

On terminating the addition, the mixture is kept for a further 1 hour under reflux, after which 10 g of 5-methyl-5,6-dihydro-11H-dibenzo (b,e) azepine-6,11-dione dissolved in 100 ml of anhydrous THF are added a little at a time. After heating the mixture under reflux for 1 hour, it is poured into water, extracted with ethyl ether, the ether removed under reduced pressure, and the product crystallised from ethanol to give a M.P. of 200°-202° C.

EXAMPLE 3

5-methyl-10-acetamino-5,6-dihydro-11H-dibenzo (b,e) azepine-6,11-dione 2 ml of acetic anhydride are added to 2.5 g of 10-amino-5,6-dihydro-11H-dibenzo (b,e) azepine-6,11-dione (prepared from 1-amino-anthraquinone in accordance with Caronna and Palazzo—Gaz. Chim. It. 83, 533, 1953) in 50 ml of dioxane. After maintaining for 2 hours under reflux, the mixture is evaporated almost to dryness under reduced pressure, the residue is then poured into water, filtered and dried to give 2 g of crude product.

The 2 g of previously obtained crude product is suspended in 20 ml of N,N-dimethylformamide, and 710 mg of sodium methylate in 10 ml of methanol are added. After maintaining for 30 minutes at ambient temperature, 2.5 ml of methyl iodide are added, and ambient temperature is maintained for 24 hours after which the mixture is poured into water, the product filtered off, dried and crystallised from ethanol, to give a M.P. of 199°-201° C.

EXAMPLE 4

11-ethoxy-5-methyl-5,6-dihydro-11H-dibenzo (b,e) azepin-6-one 18 ml of thionyl chloride are added to 7.1 g of 11-hydroxy-5-methyl-5,6-dihydro-dibenzo (b,e) azepin-6-one in 180 ml of chloroform, and the mixture is left at rest at ambient temperature for 12 hours. On removing the solvent and excess thionyl chloride under vacuum, a residue is left having a M.P. of 167°-8° C.

1.20 g of sodium ethylate in 100 ml of absolute ethanol are added a little at a time to 5.5 g of the previously obtained crude product in 56 ml of dioxane. After 2 hours of heating under reflux, the mixture is allowed to cool, filtered, the product evaporated to dryness and taken up in petroleum ether.

The product obtained is crystallised from hexane/cyclohexane (3:1) to show a M.P. of 98°-100° C.

EXAMPLE 5

[5-methyl-5,6-dihydro-6-one-11H-dibenzo (b,e) azepin-11-ylidene]ethyl acetate 5 ml of triethylphosphonium acetate are added at ambient temperature to 0.75 g of 80% sodium hydride in 100 ml of anhydrous THF. After adjusting the temperature to 10° C., 6 g of 5-methyl-5,6-dihydro-11H-dibenzo (b,e) azepine-6,11-dione dissolved in 100 ml of anhydrous THF are added a little at a time. On completion of the addition, the temperature is returned to ambient, and the mixture is kept for a further 2 hours under stirring. It is concentrated, poured into water and extracted with ethyl ether. On removing the solvent under reduced pressure, a residue is obtained which, when crystallised from cyclohexane has a M.P. of 123°-5° C.

Compositions in accordance with the present invention can be presented in a form suitable for oral, rectal or parenteral administration. They can be presented for example in the form of tablets, pills, sugar-coated pills, capsules, suspensions, oral or injectable solutions, or powders. The carriers or excipients conventionally accepted for pharmacological use can be used. The compositions are preferably presented in the form of a single dose.

The therapeutic dose of the compounds depends on the body weight, age and method of administration but generally lies between 5 mg and 2000 mg/day.

Biological activity

The compounds according to the present invention are of pharmacological interest, particularly because of their anticonvulsant-sedative activity.

The products according to the present invention were tested in the mouse and rat by the methods individually indicated in order to evalute their antagonism towards convulsions induced by MES (Swinyard et al., J. Pharm. Exp. Therap. 106, 319, 1952), by Metrazol (Krall et al., Epilessia 19, 409, 1978) and by bicuculline (Lippa, Biochem. Behav. 11, 99, 1979). In the case of some of the aforesaid products, antagonism is present even 30 minutes after administration, and continues for a number of hours.

The products are active in potentiating catalepsy induced by haloperiodol (Melville et al., Brit. J. Pharmacol. 66, 123 P, 1979), and are also active in the traction test (Biosser and Simon, Therapie XV, 1170, 1960) and in reducing tremor induced by LON 954 (Coward et al., Arzn. Forsch. 27, 2326, 1977) and that induced by oxotremorine (Spencer, Life Science 5, 1015, 1965). Antinociceptive activity was tested by the method of Hendershot and Forsaith (J. Pharm. Exp. Therap. 125, 237, 1959), and protection against hemorrhage induced by polymyxin was determined in accordance with BEL, Le Journal de Medecin de Lyon 1667, 1969.

The compounds according to the present invention demonstrated an $LD_{50}$ greater than or equal to 2000 mg/kg for oral administration in the mouse and rat.

We claim:

1. A compound of the formula:

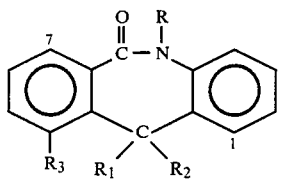

in which R is hydrogen or alkyl containing 1 to 4 carbon atoms, $R_1$ and $R_2$ jointly represent an oxygen atom, and $R_3$ is NHCO-lower alkyl, NHCO-phenyl, NHCONH-lower alkyl or NHCONH-phenyl.

2. A compound of claim 1 wherein such compound is 10-acetamino-5,6-dihydro-11H-dibenzo(b,e) azepine-6,11-dione.

3. A compound of claim 1 wherein such compound is N-methyl-N'-[5,6-dihydro-6,11-dione-11H-dibenzo(b,e) azepine-10-yl] urea.

4. A compound of claim 1 wherein such compound is 10-acetamino-5-methyl-5,6-dihydro-11H-dibenzo(b,e) azepine-6,11-dione.

5. A compound of claim 1 wherein such compound is 10-benzoylamino-5,6-dihydro-11H-dibenzo(b,e) azepine-6,11-dione.

6. A compound of claim 1, wherein such compound is N-phenyl-N'-[5,6-dihydro-6,11-dione-11H-dibenzo(b,e) azepine-10-yl] urea.

7. A compound of claim 1, wherein such compound is 10benzoylamino-5-methyl-5,6-dihydro-11H-dibenzo(b,e) azepine-6,11-dione.

8. A pharmaceutical composition comprising as active principle an anti-convulsant or sedative amount of at least one compound of claim 1, in proportional association with a corresponding pharmaceutical administration amount of a pharmaceutical carrier or excipient.

9. A pharmaceutical composition comprising as active principle an anti-convulant or sedative amount of at least one compound of the formula

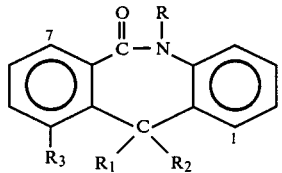

in which R is hydrogen or alkyl containing 1 to 4 carbon atoms, $R_1$ and $R_2$ which can be different represent hydrogen, hydroxy, alkyl containing 1 to 8 carbon atoms, alkoxy containing 1 to 8 carbon atoms or phenyl lower alkyl, or can jointly represent an oxygen atom or a $CHCOOR_1'$ group where $R_1'$ is hydrogen or alkyl containing 1 to 4 carbon atoms, and $R_3$ is hydrogen, $NH_2$, NHCO-lower alkyl, NHCO-phenyl, NHCONH-lower alkyl or NHCONH-phenyl, in proportional association with a corresponding pharmaceutical administration amount of a pharmaceutical carrier or excipient.

10. Composition of claim 9 wherein $R_1$ and $R_2$ which can be different represent hydrogen, hydroxy, alkyl containing 1 to 8 carbon atoms, alkoxy containing 1 to 8 carbon atoms or phenyl lower alkyl, or can jointly represent an oxygen atom.

11. Composition of claim 9 wherein $R_1$ and $R_2$ which can be different, represent hydrogen, hydroxy, alkyl containing 1 to 8 carbon atoms, alkoxy containing 1 to 8 carbon atoms or benzyl, or can jointly represent an oxygen atom or a $CHCOOR_1'$ group where $R_1'$ is hydrogen or alkyl containing 1 to 4 carbon atoms, and $R_3$ is hydrogen, $NH_2$, NHCO-methyl, NHCO-phenyl, NHCONH-methyl or NHCONH-phenyl.

12. Composition of claim 9 in a form suitable for oral, parenteral or rectal administration.

13. Composition of claim 9 in the form of a single dose.

14. A pharmaceutical composition comprising as active principle an anti-convulsant or sedative amount of at least one compound of the formula

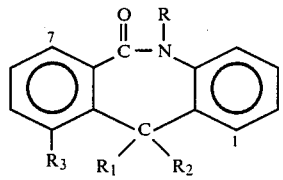

in which R is methyl, $R_1$ and $R_2$ which can be different represent hydrogen, hydroxy, alkyl containing 1 to 8 carbon atoms, alkoxy containing 1 to 8 carbon atoms or phenyl lower alkyl, and $R_3$ is hydrogen, in proportional association with a corresponding pharmaceutical administration amount of a pharmaceutical carrier or excipient.

15. Composition of claim 14 wherein such compound is 5,11-dimethyl-11-hydroxy-5,6-dihydro-11H-dibenzo (b,e) azepine-6-one.

16. Composition of claim 14 wherein such compound is 5-methyl-11-ethoxy-5,6-dihydro-11H-dibenzo(b,e) azepine-6-one.

17. Composition of claim 14 wherein such compound is 11-benzyl-11-hydroxy-5-methyl-5,6-dihydro-11H-dibenzo(b,e) azepin-6-one.

18. Composition of claim 14 wherein such compound is 11-octyloxy-5-methyl-5,6-dihydro-11H-dibenzo(b,e) azepine-6-one.

* * * * *